United States Patent
Braun

(10) Patent No.: US 11,826,278 B2
(45) Date of Patent: Nov. 28, 2023

(54) DEVICE FOR THE EXTRACORPOREAL CONTROLLING OF THE TEMPERATURE OF PATIENTS, HAVING A SEPARABLE SECONDARY UNIT

(71) Applicant: LAUDA DR. R. WOBSER GMBH & CO. KG, Lauda-Königshofen (DE)

(72) Inventor: Kristofer Braun, Bad Mergentheim (DE)

(73) Assignee: LAUDA DR. R. WOBSER GMBH & CO. KG, Lauda-Königshofen (DE)

( * ) Notice: Subject to any disclaimer, the term of this patent is extended or adjusted under 35 U.S.C. 154(b) by 874 days.

(21) Appl. No.: 16/679,405

(22) Filed: Nov. 11, 2019

(65) Prior Publication Data
US 2020/0146877 A1     May 14, 2020

(30) Foreign Application Priority Data

Nov. 9, 2018 (DE) .......................... 102018128102.1

(51) Int. Cl.
*A61F 7/00* (2006.01)
(52) U.S. Cl.
CPC .... *A61F 7/0085* (2013.01); *A61F 2007/0069* (2013.01)
(58) Field of Classification Search
CPC .......... A61F 2007/0069; A61F 7/0085; A61M 1/1698; A61M 1/369; A61M 2205/366; F28D 2021/005; F28D 9/0037; F28F 13/12; F28F 3/083; F28F 3/12
See application file for complete search history.

(56) References Cited

U.S. PATENT DOCUMENTS

| | | |
|---|---|---|
| 4,156,459 A | 5/1979 | Kusuda et al. |
| 2009/0235686 A1 | 9/2009 | Kikuchi |
| 2009/0255655 A1 | 10/2009 | Martin et al. |
| 2011/0040359 A1 | 2/2011 | Harris et al. |
| 2011/0213305 A1* | 9/2011 | Jonsson ................ F28D 9/0075 604/113 |
| 2015/0230975 A1 | 8/2015 | Dabrowiak et al. |

(Continued)

FOREIGN PATENT DOCUMENTS

EP     0905353 A1     3/1999

OTHER PUBLICATIONS

European search report for patent application No. 19 20 7150.4 dated Mar. 10, 2020.

(Continued)

*Primary Examiner* — Tigist S Demie
(74) *Attorney, Agent, or Firm* — Bachman & LaPointe, P.C.

(57) ABSTRACT

Device for the extracorporeal controlling of the temperature of patients by transmitting heat between a fluid and a transmission medium, having a primary circuit having a primary unit (102, 201) for receiving the fluid, and a secondary circuit having a secondary unit (104, 200) which includes connectors (240, 242) for infeeding and outfeeding the transmission medium, wherein the secondary unit (104, 200) is capable of being fastened to the primary unit (102, 201) and has nozzles (206) for configuring an impingement flow, said nozzles (206), in the case of a secondary unit (104, 200) being fastened to the primary unit (102, 201), being directed in the direction of the primary unit (102, 201).

14 Claims, 3 Drawing Sheets

(56) References Cited

U.S. PATENT DOCUMENTS

2016/0082175 A1    3/2016  Jonsson et al.
2016/0287432 A1*  10/2016  Dabrowiak ........... F28D 9/0062
2018/0003451 A1*  1/2018  Azar ................. H05K 7/20254
2018/0207027 A1*  7/2018  Diller ........................ A61F 7/02
2019/0301809 A1*  10/2019  Cook ........................ F28F 3/12

OTHER PUBLICATIONS

European office action or patent application No. 19 207 150.4 dated Sep. 9, 2021.
Office Action dated Feb. 24, 2023 for corresponding EP Application 19207150.4.

* cited by examiner

DEVICE FOR THE EXTRACORPOREAL CONTROLLING OF THE TEMPERATURE OF PATIENTS, HAVING A SEPARABLE SECONDARY UNIT

FIELD OF THE INVENTION

The invention relates to a device, to a secondary unit for use in the device, and to a method for the extracorporeal controlling of the temperature of patients.

PRIOR ART

Methods and devices which are characterized by the use of heat exchangers are known for the extracorporeal controlling of the temperature of patients. In the case of heat exchangers, water is in many cases used as the medium for transporting heat or cold.

However, solutions in the prior art known to date have restrictions in terms of the thermal output capable of being transmitted, or are complex in terms of cleaning.

DISCLOSURE OF THE INVENTION

The invention is based on the object of offering an improved device for the extracorporeal controlling of the temperature of patients. The intention is to improve in particular hygiene, or the thermal output capable of being transmitted is to be improved, or the construction is to be simplified or be easier to clean, or else the adherence to hygiene standards is to be facilitated.

According to one aspect of the invention a device for the extracorporeal controlling of temperature of patients by transmitting heat between a fluid and a transmission medium is provided, wherein the device comprises a primary circuit having a primary unit for receiving the fluid, and a secondary circuit having a secondary unit which in turn comprises connectors for infeeding and outfeeding the transmission medium, wherein the secondary unit is capable of being fastened to the primary unit and has nozzles for configuring an impingement flow, said nozzles, in the case of a secondary unit being fastened to the primary unit, being directed in the direction of the primary unit.

One further aspect of the invention relates to a secondary unit, in particular adapted for use in one of the typical devices having a primary unit described herein, for example for fastening to a primary unit described herein so as to configure a heat exchanger.

One further aspect of the invention relates to a method for the extracorporeal controlling of temperature of patients by transmitting heat between a fluid and a transmission medium.

A flow which is typically created when a fluid exits through a nozzle such as, for example, a slot or a bore, and impact a flow obstacle is referred to as an impingement flow herein. A widening of the impact jet takes place in the region of the free jet of the impact jet, since the latter is influenced by the fluid already present downstream. The potential of the core of the impact jet herein becomes increasingly smaller as the spacing from the nozzle increases. The jet in the region of the dam flow is influenced by a flow obstacle such as, for example, a face, a plate, or a wall, and is laterally deflected by the flow obstacle. Turbulent or laminar flows can typically be implemented. The heat transmission takes place substantially in the center of the impact jet in the dam flow region and decreases laterally. In one typical embodiment, the device has a primary unit. The primary unit is typically part of a primary circuit in which a fluid is receivable. The fluid is typically a liquid or a gas, or gas/liquid mixture, which is suitable for storing and transmitting heat, for example water, vegetable oil, ammonia, carbon dioxide, hydrocarbons, inorganic coolants, or air. The term heat, or transmission of heat, herein is also understood to be cold, or the transmission of cold. The terms "heat" and "transmission of heat" herein are understood in a physical context.

The primary unit typically has a barrier element for transmitting heat to the transmission medium. The transmission medium is typically a liquid. The transmission medium in typical embodiments comprises at least 90% by weight or at least 95% by weight water, in particular water for injection (WFI). In one typical embodiment the transmission medium is a physiological or isotonic medium. The transmission medium is typically sterile or largely aseptic, for example fewer than 1000 or at most 100 colony-forming aerobic bacteria per liter. Physiological or isotonic media are, for example, a 0.9% saline solution (sodium chloride, NaCl), or a Ringer's solution.

The primary unit typically has a barrier element which comprises a plate or is configured as a plate. In one typical embodiment the plate has a flat or a smooth surface. The plate can typically be structured. Further typical embodiments include curved plates or generally curved surfaces which form the barrier element.

The plate is typically from a metal or a metal alloy, for example a titanium alloy or an alloy comprising iron. In further embodiments the plate comprises a ceramic material. In one typical embodiment the plate is made from a metal which is suitable for transmitting heat. The plate is typically disposed on one side of the primary unit. The plate on the primary unit is typically accessible from the outside. The plate in typical embodiments forms an external side of the primary unit. In further embodiments, a removable protective plate can be configured in front of the plate. Further embodiments include primary units which have barrier elements, for example plates or radiused surfaces, on a plurality of sides.

In one typical embodiment the secondary unit has a seal which seals a secondary unit fastened to the primary unit in relation to the barrier element. The secondary unit typically has at least one of the following seals: a labyrinth seal, a gap seal, a seal from a sealing material such as, for example, plastics material, metal, or organic and/or inorganic materials, a flat seal, or a materially integral seal. The seal is typically embodied on the secondary unit. In one typical embodiment the seal is embodied on the primary unit or as an independent element.

In one typical embodiment the secondary unit is separable from the primary unit, or is capable of being in particular repeatedly fastened to the primary unit. The secondary unit is typically separable from the primary unit without damage. In one typical embodiment the secondary unit is capable of being repeatedly separated from the primary unit. First and second secondary units are typically separable or separable without damage from the primary unit, wherein first and second secondary units can be constructed so as to be mutually dissimilar or identical. A secondary unit that is embodied so as to be separable from the primary unit can offer the advantage that a device or a secondary unit for use in a device is sterile.

The secondary unit is typically configured for single use. In one typical embodiment the secondary unit is configured for multiple use. In the case of a single use, the secondary unit is configured, for example, as a disposable item or as a single-use item. A reliable adherence to hygiene standards can be achieved on account thereof. In typical embodiments the secondary unit is constructed so as to be capable of autoclaving. In this way, the secondary unit can be used multiple times on account of which waste can be saved.

In one typical embodiment the secondary unit is made substantially from plastics material. The secondary unit is typically at least substantially from plastics material. The secondary unit is typically from plastics material to the extent of at least 90%, or at least 80%, or at least 70%. The indications herein refer to % by weight. The secondary unit is typically from plastics material to an extent of less than 100%, or less than 50%. In one typical embodiment the secondary unit is from metal, at least to the extent of substantially 100%. The secondary unit is typically from metal to the extent of at least 90%, or at least 80%, or at least 70%. The secondary unit is typically from metal to the extent of less than 100%, or less than 50%.

In one typical embodiment the device has a connection element for releasably fastening the secondary unit to the primary unit. Typical connection elements can include a bayonet closure that is configured on the primary unit and the secondary unit, or clamps or threads. A rapid assembly or disassembly of the secondary unit without damage is possible in this way.

The barrier element typically has a heat exchanger. In one typical embodiment the barrier element is embodied in two parts, wherein a first sub-element of the barrier element is a plate, and a second sub-element has structures which permit the fluid of the primary circuit to flow through. The first and the second sub-element of the barrier element are typically connected in a materially integral or form-fitting manner. In one typical embodiment the barrier element is embodied in one part, wherein the barrier element has structures which permit the fluid to flow through. The barrier element is typically suitable for transmitting heat. In one typical embodiment the fluid of the primary circuit comprises water ($H2O$), vegetable or mineral oil, ammonia, carbon dioxide, hydrocarbons, or inorganic coolants.

In one typical embodiment a secondary unit is provided for use in a typical device described herein for the extracorporeal controlling of temperature of patients.

The secondary unit typically comprises a first chamber having a first connector for infeeding the transmission medium to the first chamber, and a second chamber having a second connector for outfeeding the transmission medium from the second chamber, wherein the second chamber has an open side. Typical secondary units have at least one open side. The nozzles of the secondary unit are typically aligned in the direction of the open side.

In one typical embodiment the first chamber of the secondary unit and the second chamber of the secondary unit are connected by at least one nozzle or by a plurality of nozzles that for directing a flow of the transmission medium to the open side is/are directed toward the open side of the second chamber.

At least one of the nozzles typically has a round cross-section. In typical embodiments at least one of the nozzles has an angular or an elongate cross section. In one typical embodiment the at least one nozzle is embodied as a Venturi nozzle. The first and the second chamber of the secondary unit are typically connected to one another by way of at least two, at least 10, or at least 100 nozzles. The first and the second chamber of the secondary unit are typically connected to one another by fewer than 1000 nozzles, fewer than 500 nozzles.

At least some or all of the nozzles which connect the first chamber and the second chamber of the secondary unit are typically disposed as a nozzle array. In typical embodiments the nozzles are disposed in a random manner.

In typical embodiments the first chamber of the secondary unit comprises a filter mesh. The filter mesh is typically disposed ahead of, thus upstream of, at least one or all of the nozzles. The filter mesh is typically disposed such that a fluid first flows through the filter mesh before said fluid makes its way to a nozzle. The filter mesh is typically disposed such that clogging of the nozzles can be prevented. The filter mesh can offer the advantage that the operational reliability is increased.

In typical embodiments the secondary circuit has at least one device for eliminating air bubbles. Residual air from the secondary circuit can be passively removed in this way while filling the secondary circuit with the transmission medium.

In typical embodiments a method for the extracorporal controlling of the temperature of patients by a primary circuit having a primary unit for receiving the fluid and a secondary circuit having a secondary unit which comprises connectors for infeeding and outfeeding the transmission medium comprises the following steps: fastening a first secondary unit to the primary unit; controlling the temperature of a first transmission medium in the first secondary unit by means of the fluid guided through the primary unit; separating the first secondary unit from the primary unit while optionally removing the first transmission medium; cleaning the primary unit, in particular cleaning at least the region of the barrier element that has been in contact with the first transmission medium; fastening a second secondary unit to the primary unit; controlling the temperature of a second transmission medium in the second secondary unit by means of the fluid guided through the primary unit; separating the second secondary unit from the primary unit.

The second transmission medium is typically removed before or after the separation of the second secondary unit. In typical embodiments, cleaning of the primary unit, in particular cleaning at least the region of the barrier element that has been in contact with the second transmission medium, is performed after the separation. The method can subsequently be continued with a third and, in analogous manner, further secondary units and a third and, in an analogous manner, further transmission media. A replacement of the secondary unit, or an autoclaving of the secondary unit, and a removal, thus typically a disposal of, the transmission medium is typically performed after each controlling of the temperature of a patient. Hygiene standards can be readily adhered to in this way. The transmission of heat between the fluid and the transmission medium is typically based on the impingement flow principle.

The barrier element typically has an area of at least 0.01 m*m, at least 0.02 m*m, at least 0.03 m*m, at least 0.04 m*m, or at least 0.2 m*m. In typical embodiments the barrier element has an area of less than 10 m*m, of less than 5 m*m, or less than 1 m*m, or less than 0.5 m*m, or less than 0.1 m*m. In this way sufficient thermal outputs of the device for controlling the temperature of a patient can be reliably achieved by way of a compact device. In typical embodiments the barrier element can have a structured surface such as, for example, having ribs or microstructures.

BRIEF DESCRIPTION OF THE DRAWINGS

Exemplary embodiments of the invention will be explained in more detail hereunder by means of drawings in which.

DESCRIPTION OF THE EXEMPLARY EMBODIMENTS SHOWN IN THE FIGURES

Typical exemplary embodiments of the invention will be described hereunder, wherein the same reference signs are used for identical or similar parts and are not explained once again in the context of each figure. The invention is not limited to the typical embodiments described hereunder.

Figure 1:
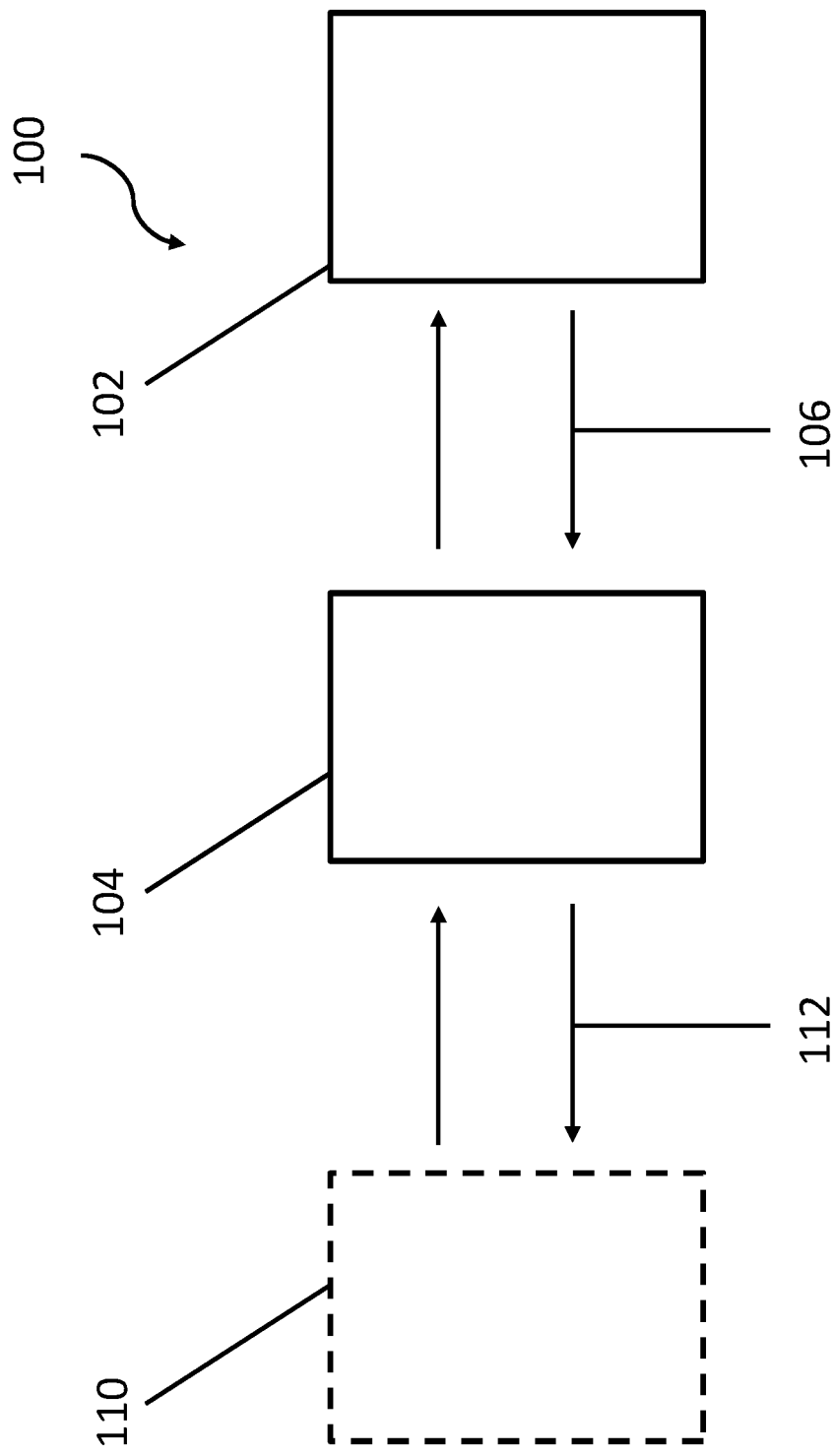
FIG. 1 shows a schematic construction of the device having a primary unit and a secondary unit.

A typical embodiment of the device 100 is schematically shown in FIG. 1. The device 100 typically comprises a primary circuit which is provided for thermal transportation and has a primary unit 102, and a secondary circuit which is provided for thermal transportation and has a secondary unit 104.

The primary circuit having the primary unit 102 transmits heat 106 to the secondary unit 104. As is generally the case in this application, this wording also includes a transportation of heat in the opposite direction, that is to say cooling. The heat transmission 106 is typically implemented by way of one nozzle or a plurality of nozzles which configures/configure an impingement flow. The secondary circuit by means of a transmission medium, in the example illustrated by means of a 0.9% NaCl solution (isotonic solution) transmits heat 112 from the secondary unit 104 to an oxygenator 110 in which the heat can be transmitted to the blood of a patient. Again, as is the case anywhere in this application, the term "transmitting heat" also includes an extraction of heat, thus cooling. In this way, a patient whose blood circulation is at least in part guided through the oxygenator 110 can be controlled in terms of temperature, that is to say be cooled or heated.

Figure 2:
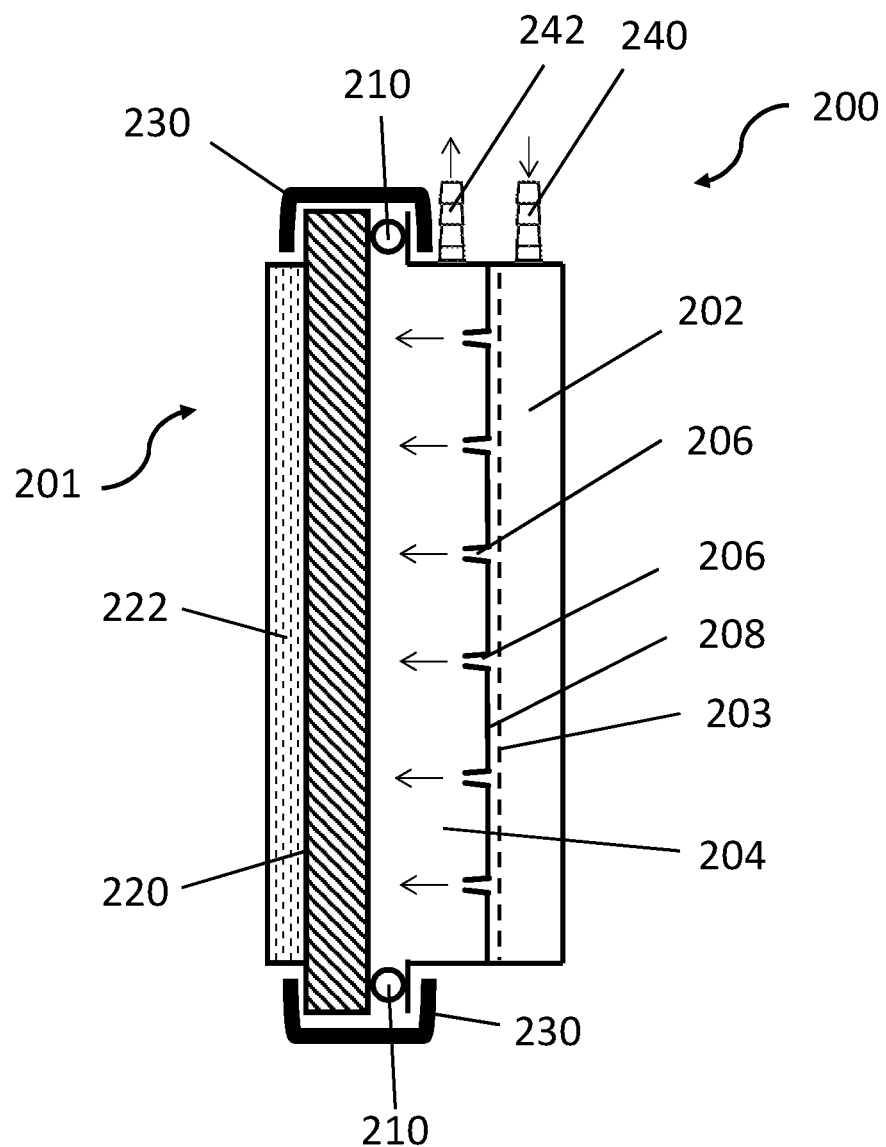
FIG. 2 shows a schematic section through a secondary unit having a first chamber and a second chamber, wherein the secondary unit is separably connected to a primary unit.

A schematic section through a typical secondary unit 200 is shown in a lateral view in FIG. 2. The secondary unit 200 is separably connected to a primary unit 201.

The secondary unit 200 comprises a first chamber 202 having a connector 240 for the infeeding of a transmission medium, and a second chamber 204 having a connector 242 for the out outfeeding of the transmission medium. The first chamber 202 of the secondary unit 200 comprises a filter mesh 203.

The first chamber 202 is connected to the second chamber 204 by nozzles 206 which are disposed so as to be organized in a nozzle array 208. The filter mesh 203 is disposed such that a fluid first meets the filter mesh 203 before said fluid makes its way through the nozzles 206 into the second chamber 204; the filter mesh 203 is thus disposed upstream of the nozzles 206. The second chamber 204 has an open side. The nozzles 206 of the nozzle array 208 are directed toward the open side of the second chamber 204. The one nozzle or the plurality of nozzles typically configure in each case one impact jet.

The open side of the second chamber 204 has a seal 210 that encircles the open side. The seal 210 seals the open side of the second chamber 204 in relation to a barrier element 220 of the primary unit 201. The barrier element 220 in the exemplary embodiment shown in FIG. 2 comprises a plate, or in the illustrated typical exemplary embodiment of FIG. 2 is configured as a plate, respectively. The plate of the barrier element 220 is connected to a heat exchanger structure 222 of the primary unit 201. In typical embodiments the one impact jet or the plurality of impact jets impacts/impact the barrier element or a plate of the barrier element, and configure an impact flow.

The connection between the heat exchanger structure and the plate is typically materially integral or form-fitting. In typical embodiments the heat exchanger structure is integrated in the plate.

The heat exchanger structure 222 in the exemplary embodiment of FIG. 2 has ducts which are passed through by a flow of a fluid.

The fluid is typically controlled in terms of temperature by means of a heat exchanger of the primary circuit.

In the exemplary embodiment of FIG. 2 the barrier element 220 of the primary unit 201 is connected to a structure, for example a periphery, of the second chamber 204 of the secondary unit 200 by way of a separable connection 230 in the form of tension clamps. In typical embodiments the seal 210 is disposed on the periphery. Simple and reliable sealing is achieved in this way.

The separable connection is typically a form-fitting connection. A typical separable connection can be embodied, for example, as a bayonet closure or as tension clamps. In one typical embodiment the secondary unit is embodied so as to be round. The secondary unit can typically also be embodied so as to be angular.

The seal typically seals the secondary unit in relation to the barrier element of the primary unit. In one typical embodiment the seal laterally seals an open side of the secondary unit in relation to a barrier element of the primary unit or in relation to the primary unit. The seal is typically embodied in one part. In one typical embodiment the seal is embodied having at least two parts which seal an open side of the secondary unit in relation to an uncontrolled leakage of transmission medium.

In one typical embodiment the open side of the secondary unit has a plurality of openings. The open side of the secondary unit typically has one or a plurality of openings.

Figure 3:
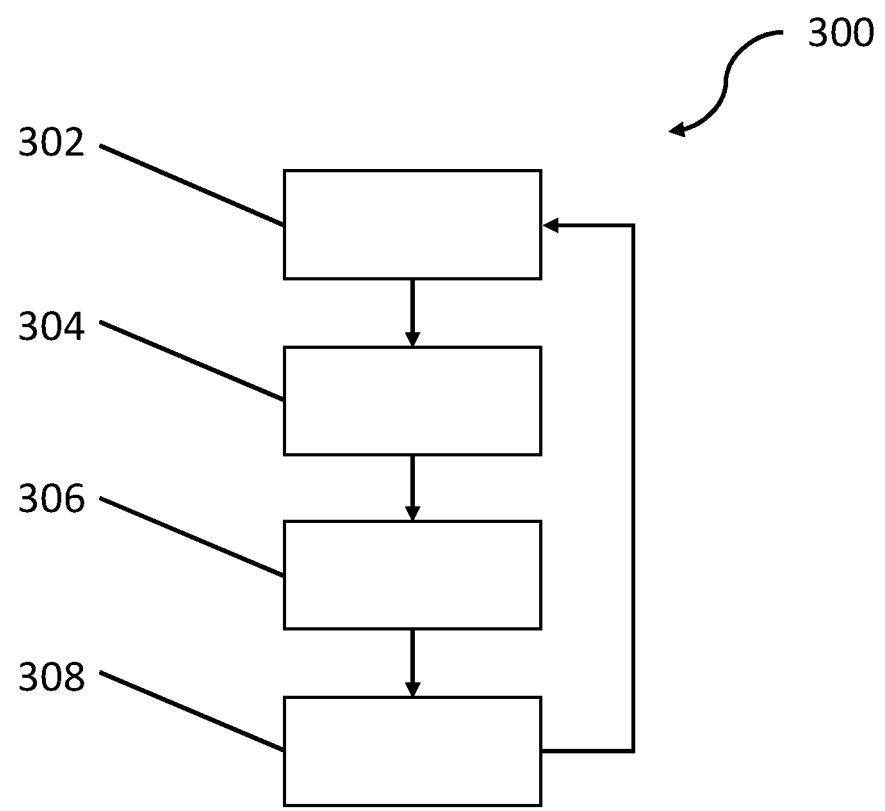
FIG. 3 shows a method in one typical embodiment.

A typical method 300 for the extracorporeal controlling of the temperature of patients by transmitting heat by means of a fluid and a transmission medium is schematically shown in FIG. 3.

In the exemplary method, 300 as shown in FIG. 3, a first secondary unit is separably connected to a primary unit in step 302. The separable connection is typically separable without damage. The separable connection is typically sealed in relation to an uncontrolled leakage of transmission medium.

A first transmission medium in the first secondary unit is controlled in terms of temperature by means of the fluid guided through the primary unit in step 304.

The first secondary unit is separated without damage from the primary unit in step 306. The barrier element of the primary unit or the primary units is cleaned in step 308. Cleaning typically includes sterilizing the primary unit or at least part of the primary unit such as, for example, the barrier element.

The method for the next patient subsequently returns back to step 302 wherein a second secondary unit and a second transmission medium are then used in the second sequence such that no bacteria introduced into the first transmission medium in the first sequence can lead to any contamination. A third sequence and further sequences of the method can be performed for controlling the temperature of further patients.

The repetition can also be performed using a sterilized secondary unit.

The invention claimed is:

1. Device for the extracorporeal controlling of the temperature of patients by transmitting heat between a fluid and a transmission medium, having
 a primary circuit having a primary unit for receiving the fluid; and
 a secondary circuit having a secondary unit, the secondary unit comprising a chamber with an open side, one or more nozzles directed in the direction of the open side, and connectors for infeeding and outfeeding the transmission medium,
 wherein the secondary unit is fastened to the primary unit such that said one or more nozzles are directed in the direction of the primary unit for an impingement flow.

2. Device according to claim 1, wherein the primary unit comprises a barrier element for transmitting heat to the transmission medium.

3. Device according to claim 2, wherein the barrier element comprises a plate.

4. Device according to claim 3, wherein the secondary unit has a seal which encloses an open side of the secondary unit and which seals the secondary unit fastened to the primary unit in relation to the barrier element.

5. Device according to claim 3, wherein the plate has a flat surface as a flow obstacle for the impingement flow.

6. Device according to claim 1, wherein the secondary unit is separable from the primary unit.

7. Device according to claim 1, wherein the secondary unit is configured for single use.

8. Device according to claim 1, wherein the secondary unit is at least substantially made from a plastics material.

9. Device according to claim 1, having a connection element for releasably fastening the secondary unit to the primary unit.

10. Device according to claim 1, wherein the barrier element has a heat exchanger.

11. Device according to claim 1, wherein the secondary unit comprises at least a first secondary unit and a second secondary unit each having the one or more nozzles, wherein each of the first secondary unit and the second secondary unit can be fastened to the primary unit
 such that the nozzles are directed in the direction of the primary unit for the impingement flow.

12. Device according to claim 11, wherein each of the first secondary unit and the second secondary unit comprises a seal that encircles the open side.

13. Method for the extracorporeal controlling of the temperature of patients by transmitting heat between a fluid and a transmission medium with the device according to claim 1, the method comprising the steps of:
 fastening the secondary unit to the primary unit;
 controlling the temperature of the transmission medium in the secondary unit by means of the fluid guided through the primary unit;
 separating the secondary unit from the primary unit;
 cleaning the primary unit;
 fastening a further secondary unit to the primary unit;
 controlling temperature of a further transmission medium in the further secondary unit by means of the fluid guided through the primary unit; and
 separating the further secondary unit from the primary unit.

14. Method according to claim 13, wherein the transmission of heat between a fluid and the transmission medium is based on the impingement flow principle.

* * * * *